US007469383B2

(12) United States Patent
Busch

(10) Patent No.: US 7,469,383 B2
(45) Date of Patent: Dec. 23, 2008

(54) MEDICAL APPARATUS FOR DIAGNOSIS OR TREATMENT

(75) Inventor: Erik Busch, Malvern, PA (US)

(73) Assignee: Siemens Aktiengesellschaft, Munich (DE)

( * ) Notice: Subject to any disclaimer, the term of this patent is extended or adjusted under 35 U.S.C. 154(b) by 624 days.

(21) Appl. No.: 10/981,263

(22) Filed: Nov. 4, 2004

(65) Prior Publication Data

US 2005/0100131 A1 May 12, 2005

(30) Foreign Application Priority Data

Nov. 6, 2003 (DE) ............................ 203 17 062 U

(51) Int. Cl.

| | |
|---|---|
| ***G06F 3/00*** | (2006.01) |
| ***G06F 3/048*** | (2006.01) |
| ***H04K 1/00*** | (2006.01) |
| ***G05B 15/00*** | (2006.01) |
| ***A61B 5/00*** | (2006.01) |

(52) U.S. Cl. ....................... 715/743; 715/707; 713/182; 700/83; 600/300

(58) Field of Classification Search ................. 715/700, 715/707, 708, 731, 751, 753, 754, 777, 2, 715/51, 741, 742, 743; 700/17, 65, 83; 600/1, 600/300; 606/1; 607/5; 128/903; 434/350; 601/41; 713/182; 725/25, 30; 726/2; 705/2, 705/51

See application file for complete search history.

(56) References Cited

U.S. PATENT DOCUMENTS

| | | | | |
|---|---|---|---|---|
| 6,269,267 | B1 * | 7/2001 | Bardy et al. | 607/5 |
| 6,292,692 | B1 * | 9/2001 | Skelton et al. | 607/5 |
| 6,398,744 | B2 * | 6/2002 | Bystrom et al. | 601/41 |
| 6,535,714 | B2 * | 3/2003 | Melker et al. | 434/350 |
| 6,589,169 | B1 * | 7/2003 | Surwit et al. | 600/300 |
| 6,609,115 | B1 * | 8/2003 | Mehring et al. | 705/51 |
| 6,801,227 | B2 * | 10/2004 | Bocionek et al. | 715/777 |
| 6,834,207 | B2 * | 12/2004 | Miyauchi et al. | 700/65 |
| 6,871,283 | B1 * | 3/2005 | Zurko et al. | 726/10 |
| 6,928,554 | B2 * | 8/2005 | Dettinger et al. | 726/19 |
| 6,934,356 | B1 * | 8/2005 | Satheesan et al. | 378/62 |
| 6,963,937 | B1 * | 11/2005 | Kamper et al. | 710/73 |
| 7,062,714 | B1 * | 6/2006 | Mo et al. | 715/731 |
| 7,080,098 | B2 * | 7/2006 | Smirniotopoulos et al. | 707/104.1 |
| 7,263,710 | B1 * | 8/2007 | Hummel et al. | 725/86 |
| 2002/0032582 | A1 * | 3/2002 | Feeney et al. | 705/2 |
| 2002/0082864 | A1 * | 6/2002 | Kelley et al. | 705/2 |
| 2003/0036683 | A1 * | 2/2003 | Kehr et al. | 600/300 |
| 2003/0065241 | A1 * | 4/2003 | Hohnloser | 600/1 |

(Continued)

OTHER PUBLICATIONS

"AXIOM Artis *d*FC and AXIOM Artis *d*BC", Siemens AG, Medical Solutions, Order No.: A91100-M1400-B151-1-7600, 24 pages, CC 64151 WS 95935, Erlangen, Germany.

*Primary Examiner*—Crystal J Barnes Bullock

(57) ABSTRACT

The invention relates to a medical apparatus for diagnosis and/or treatment using a procedure (20), with an operating console (11) to control the use of components of the procedure (20), the operating console (11) having an input device (22), an output device (27) and an assistance module (26) to assist the user, which can be adapted to users' varying levels of training. This enables the user interfaces of the operating console to be adapted to the varying levels of knowledge of the medical operating personnel, so that the user in question is offered only those commands, with corresponding additional information, which the user has for example already learned during training.

9 Claims, 2 Drawing Sheets

U.S. PATENT DOCUMENTS

2003/0135733 A1 7/2003 Heam et al.
2004/0152954 A1 * 8/2004 Pearce et al. ................ 600/300
2004/0162589 A1 * 8/2004 Bystrom et al. ................ 607/5
2004/0172558 A1 * 9/2004 Callahan et al. ............. 713/201
2005/0027560 A1 * 2/2005 Cook ............................ 705/2
2006/0089855 A1 * 4/2006 Holland et al. ................. 705/2

* cited by examiner

PRIOR ART

MEDICAL APPARATUS FOR DIAGNOSIS OR TREATMENT

CROSS REFERENCE TO RELATED APPLICATIONS

This application claims priority to the German application No. 20317062.8, filed Nov. 6, 2003 and which is incorporated by reference herein in its entirety.

FIELD OF INVENTION

The invention relates to a medical apparatus for diagnosis and/or treatment using a procedure, with an operating console to control the use of components of the procedure, said operating console having an input device and an output device.

BACKGROUND OF INVENTION

Coronary heart disease is one of the most frequent causes of death, and is on the increase. X-ray examination of the coronary blood vessels using contrast media, known as coronary angiography, enables coronary heart disease to be diagnosed using a coronary catheter. This procedure at the same time allows the coronary blood vessels to be treated using what is known as a balloon catheter (PTCA) with and without insertion of a stent (mostly wire mesh dilation). This diagnosis and treatment is performed on a left heart catheter measuring site (LHC). Such a left heart catheter measuring site is known from the brochure "AXIOM Artis dFC and AXIOM Artis dBC" from Siemens Medical Solutions, Order No.: A91100-M1400-B151-1-7600, print reference CC 64151 WS 05035, and is illustrated by way of example in FIG. 1. The LHC has a biplanar, schematically represented X-ray diagnostic apparatus 1 with two C-arms 2 and 3, at the respective ends of which X-ray emitters 4 and 5 as well as X-ray detectors 6 and 7 situated opposite in known fashion, for example flat detectors, are in-stalled. Furthermore, the X-ray diagnostic apparatus 1 is provided with a patient examination table 8. For observation of the examination a monitor support or monitor bank 9 is provided, in this example containing four monitors 10. However, a standard LHC has six displays in the examination room.

An operating console 11 is located in an adjacent control room for communication with the system for the purpose of controlling the C-arms 2 and 3, image generation and image processing. Normally an operating console 11 in the control room of an LHC is provided with two monitors.

SUMMARY OF INVENTION

However, proficient operation of such medical imaging units for the purpose of high-quality diagnosis and treatment calls for extensive specialist knowledge.

For this reason the operating personnel of the operator are given several days' intensive training by the supplier of the medical technology. During the training period these personnel are not available to the operator for routine examinations. Furthermore, because of high turnover and flexible deployment of operating personnel the requisite level of knowledge cannot always be achieved or maintained. To maintain the level of knowledge, refresher courses are required, which however once again affect the work of the operators of the systems.

In the case of emergencies and accidents this can mean that medical care cannot be guaranteed.

It is therefore an object of the invention to provide a medical apparatus of the type referred to in the introduction, such that even medical operating personnel with little training can operate the medical apparatus without difficulty.

The object is achieved by the claims. This enables the user interfaces of the operating console to be adapted to the varying levels of knowledge of the medical operating personnel, so that the respective user is offered only those commands, with corresponding additional information, which the user has for example already learned during training.

It has proved advantageous if the operating console has a sensor device to ascertain the current user.

Reliable functioning is guaranteed if the operating console has a test device which checks the current user's access rights, level of knowledge and standard of training, etc., and to which attributes characterizing the user are supplied.

Customized menus improve the transparency of user prompting and hence simplify the work of the operating personnel if the assistance module has a dynamically customizable user inter-face.

Advantageously the operating console can have a memory for user profiles, by means of which the user interface of the connected assistance module can be dynamically adapted, the memory being connected to the input device in order to change the user profiles.

According to the invention, the access to and functionality of the application software can be graduated for the purpose of diagnosis and treatment.

BRIEF DESCRIPTION OF THE DRAWINGS

The invention is described in greater detail below with the aid of an exemplary embodiment illustrated in the drawing. This shows.

DETAILED DESCRIPTION OF INVENTION

Figure 1:
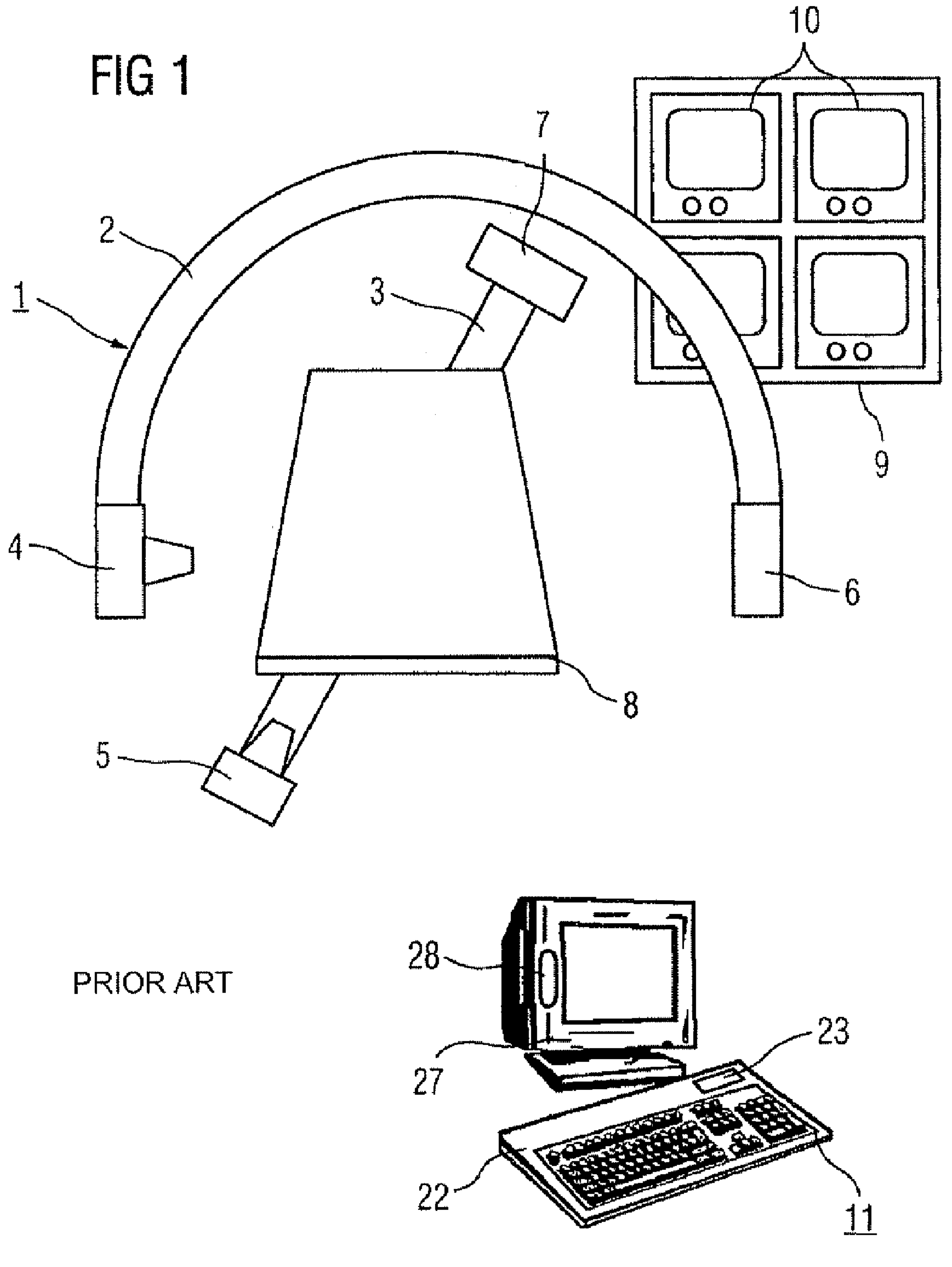
FIG. 1 a known left heart catheter measurement site (LHC)
Figure 2:
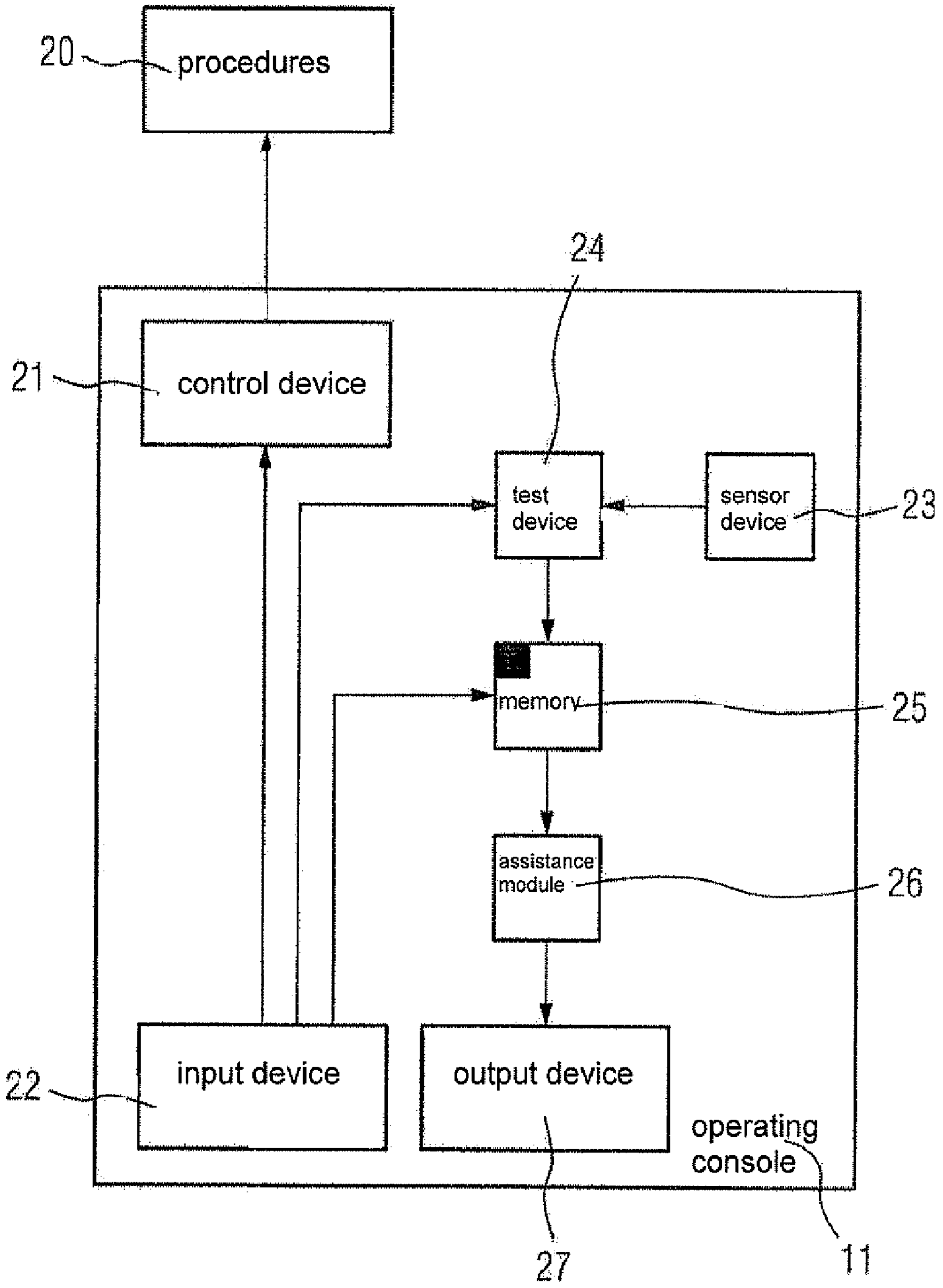
FIG. 2 an inventive operating console of the LHC as per FIG. 1.

FIG. 2 illustrates the structure of the operating console 11 in greater detail. The operating console 11 is provided with a control device 21 for procedures 20 of the system, for example the X-ray diagnostic apparatus 1. The control device 21 in connected in known fashion to an input device 22 to input the control commands.

According to the invention, the operating console 11 has a sensor device 23 to ascertain the current user. The sensor device 23 can consist of a card reader or a fingerprint sensor. However, the sensing can also be performed by entering the name and user ID via the keyboard of the input device 22.

A test device 24 is connected to the sensor device 23, and checks the current user's access rights, level of knowledge and standard of training, etc. The test device 24 is connected to a memory 25 for user profiles, by means of which the user interface of a connected assistance module 26 can be dynamically adapted. The memory 25 is connected to the input device 22 to change the user profile. The assistance module 26 is connected to an output device 27, for example a monitor.

By ascertaining and determining the current user by means of the sensor device 23 and test device 24 the operating console 11 is switched to the mode required for the level of knowledge of the current user. To this end the desired user pro-file is read out from the memory 25 and passed to the assistance module 26, which controls the user interface on the output device 27 such that only those commands are offered which the current operator can and may perform. In addition, the commands are offered with an explanation appropriate to the user's level of knowledge, so that the current user can, even without significant prior knowledge, pass the correct and requisite commands to the procedure 20 via the input device 22 and control device 21.

The user interface of the output device 27 is intelligently adapted to the user by the following three software measures:

Assistant:

The assistant in the assistance module 26 is easy to activate and enables an untrained or inexperienced person, without prior knowledge, to operate the sys-tem in an emergency, it still being possible for a specialist to intervene. The inexperienced person is prompted from input of the demographic data to storage of the image data by corresponding on-screen instructions and explanations.

Beginner and Expert Mode:

The functionality of the imaging system, for example an angiocardiography system, is offered in graduated form. Use of the next stage can be made dependent on further training.

Customized Menus:

Functions employed only rarely by a user are automatically not displayed, but can easily be called up again.

The inventive design of the operating console 11 for special medical systems thus provides a solution enabling the user interface of the operating console 11 to be adapted to the level of knowledge of the medical operating personnel and ensuring operation even in exceptional situations.

The graduated performance of the functional scope of the system, in conjunction with the requisite further training, cuts the risk of incorrect operation and can highlight the level of knowledge of the operating personal and hence assist the operator's training strategy.

The customized menus improve the transparency of user prompting and hence simplify the work of the operating personnel.

The operating console 11 is distinguished by the following points which are essential for the invention:

- an assistant assists the operator of the medical system,
- the user interface is dynamic and can be customized and
- graduated access to the application software for the purpose of diagnosis and treatment is possible, and hence graduated functionality.

Commands can be output from the output device 27

- visually, e.g. via displays on the monitor of the operating console 11 or projection,
- visually, e.g. by printing out on print media of a printer,
- acoustically, e.g. by sound modulation (voice) using a loudspeaker 28 of the operating console 11 and/or
- sensorially, e.g. via a Braille output device arranged on the operating console 11.

The inventive design of the medical apparatus for diagnosis and/or treatment resolves the contradiction between, on the one hand, a lack of information in specific situations, and on the other hand the availability of a learning and information system in the form of the PC, device computer or operating console which can effectively support on-the-job learning (just in time) and provide selective information at the specifically require d moment.

The invention claimed is:

1. A medical apparatus for executing a medical procedure, comprising:

an application device for executing the medical procedure having a plurality of application components;

an operating console for controlling the application components;

an input device for inputting a control command;

an output device for displaying a graphic user interface; and an assistance module adapted to support a user for operating the medical apparatus according to a level of competence of the user;

a control function configured in conjunction with the assistance module to control a user's access rights, and thereby vary and limit the user's ability to operate the device with the application components, based on a profile of the user so that, given multiple levels of access, access by a user to operate the device with the application components is limited to a level consistent with information in the profile, such that different users may be provided with different levels of access to control or operate and wherein when access is made available to a user the apparatus is configured to a mode of operation corresponding to a designated level for that user.

2. The medical apparatus according to claim 1, wherein the medical procedure includes an element chosen from the group consisting of acquiring medical data related to bodily functions, diagnosis of a medical condition and treatment of a medical condition of a patient and wherein access by a user to operate the device with the application components is limited to a level consistent with information in the profile corresponding to a level of knowledge of the user, such that different users may be provided with different levels of access to operate the device based on level of knowledge of each user.

3. The medical apparatus according to claim 1, wherein the assistance module includes a plurality of support data sets adapted to be displayed on the output device corresponding to a plurality of levels of competence.

4. The medical apparatus according to claim 1, wherein the operating console includes a sensor device for verifying the user.

5. The Medical apparatus according to claim 1, wherein the operating console includes a checking device for checking an access authorization, a skill level, and the competence level of the user using a data set representing the user.

6. The medical apparatus according to claim 1, wherein the graphic user interface is adapted to change a user-related screen displayed on the graphic user interface based on a data set representing the user.

7. The medical apparatus according to claim 1, wherein the operating console includes a memory device connected to the input device, the memory device having a plurality of stored user profiles for dynamically adapting the graphic user interface according to a current user profile input via the input device.

8. The medical apparatus according to claim 1, wherein a functionality of an application software for executing the medical procedure includes a hierarchy of function levels.

9. The medical apparatus according to claim 8, wherein the assistance module is adapted to determine a function level according to a current user profile.

* * * * *